(12) United States Patent
Wizel et al.

(10) Patent No.: US 6,849,736 B2
(45) Date of Patent: Feb. 1, 2005

(54) CRYSTALLINE FORMS OF VALACYCLOVIR HYDROCHLORIDE

(75) Inventors: Shlomit Wizel, Petah Tiqva (IL); Judith Aronhime, Rehovot (IL); Valerie Niddam-Hildesheim, Even-Yeouda (IL); Ben-Zion Dolitzky, Petach Tiqva (IL); Marina Yu Etinger, Nesher (IL); Michael Yuzefovich, Haifa (IL); Gennady A. Nisnevich, Haifa (IL); Boris Pertsikov, Nesher (IL); Boris Tishin, Haifa (IL); Dina Blasberger, Raanana (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/236,729

(22) Filed: Sep. 6, 2002

(65) Prior Publication Data

US 2003/0114470 A1 Jun. 19, 2003

Related U.S. Application Data

(60) Provisional application No. 60/317,850, filed on Sep. 7, 2001, provisional application No. 60/342,273, filed on Dec. 21, 2001, provisional application No. 60/386,505, filed on Jun. 5, 2002, and provisional application No. 60/403,838, filed on Aug. 14, 2002.

(51) Int. Cl.$^7$ ................... C07D 473/18; A61K 31/522
(52) U.S. Cl. ......................................... 544/276
(58) Field of Search .................. 544/276; 514/263.38

(56) References Cited

U.S. PATENT DOCUMENTS

| | | | | |
|---|---|---|---|---|
| 4,199,574 A | | 4/1980 | Schaeffer | |
| 4,957,924 A | * | 9/1990 | Beauchamp | 544/276 |
| 5,756,736 A | * | 5/1998 | Arzeno et al. | 544/276 |
| 5,840,890 A | * | 11/1998 | Arzeno et al. | 544/276 |
| 5,840,891 A | * | 11/1998 | Nestor et al. | 544/276 |
| 6,040,446 A | * | 3/2000 | Dvorak et al. | 544/276 |
| 6,107,302 A | * | 8/2000 | Carter et al. | 544/276 |
| 2003/0153757 A1 | * | 8/2003 | Etinger et al. | 544/276 |

FOREIGN PATENT DOCUMENTS

| | | | | |
|---|---|---|---|---|
| WO | WO 9725989 A1 | * | 7/1997 | A61K/31/52 |
| WO | WO 9727194 A1 | * | 7/1997 | C07D/473/00 |
| WO | WO 9803553 A1 | * | 1/1998 | C07D/473/00 |

OTHER PUBLICATIONS

Goodman & Gilman's, The Pharmacological Basis of Therapeutics, pp. 1193–1198 (9$^{th}$ ed. 1996).

G.M. Wall, "Pharmaceutical Applications of Drug Crystal Studies," Pharmaceutical Manufacturing, vol. 3, No. 2, Feb. 1986, pp. 33–42.

J. Haleblian and W. McCrone, "Pharmaceutical Applications of Polymorphism," Journal of Pharmaceutical Sciences, vol. 58, No. 8, Aug. 1969, pp. 911–929.

J.K. Haleblian, "Characterization of Habits and Crystalline Modification of Solids and Their Pharmaceutical Applications," Journal of Pharmaceutical Sciences, vol. 64, No. 8, Aug. 1975, pp. 1269–1288.

Pharmacopeial Forum, vol. 24, No. 1, (Jan.–Feb. 1998) p. 5438–5440.

* cited by examiner

Primary Examiner—Mark L. Berch
(74) Attorney, Agent, or Firm—Kenyon & Kenyon

(57) ABSTRACT

Provided are novel polymorphs and pseudopolymorphs of valacyclovir hydrochloride and pharmaceutical compositions containing these. Also provided are methods for making the novel polymorphs and pseudopolymorphs, which include valacyclovir hydrochloride monohydrate and valacyclovir hydrochloride dihydrate.

26 Claims, 10 Drawing Sheets

CRYSTALLINE FORMS OF VALACYCLOVIR HYDROCHLORIDE

CROSS-REFERENCE TO RELATED APPLICATIONS

This application claims the benefit of the following U.S. Provisional Applications: No. 60/317,850, filed Sep. 7, 2001; No. 60/342,273, filed Dec. 21, 2001; No. 60/386,505, filed Jun. 5, 2002; and No. 60/403,838, filed Aug. 14, 2002.

FIELD OF THE INVENTION

The present invention relates to novel crystalline forms (polymorphs and pseudopolymorphs) of the antiviral compound valacyclovir hydrochloride, and methods for obtaining them.

BACKGROUND

Valacyclovir is an L-valyl ester prodrug of acyclovir. Acyclovir is an acyclic analog of a natural nucleoside which has been found to have high anti-viral activity. Acyclovir is widely used in the treatment and prophylaxis of viral infections in humans, particularly infections caused by the herpes group of viruses. See Goodman and Gilman's, *The Pharmacological Basis of Therapeutics* 1193–1198 (9th ed. 1996).

Acyclovir is an acyclic guanine nucleoside analog that lacks a 3'-hydroxyl on the side chain. Acyclovir has the chemical name 6H-Purin-6-one, 2-amino-1,9-dihydro-9-[(2-hydroxyethoxy)methyl]. (CAS Registry No. 59277-89-3.) Acyclovir as the sodium salt is currently marketed as ZOVIRAX®. The chemical structure of acyclovir is shown as Formula I.

Formula I

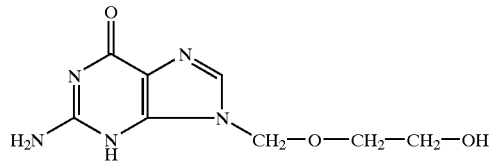

Valacyclovir has the chemical name I-valine, 2-[(2-amino-1,6-dihydro-6-oxo-9H-purin-9-yl)methoxy]ethyl ester. (CAS Registry No. 124832-26-4.) Valacyclovir is currently marketed as VALTREX®. The chemical structure of valacyclovir is shown as Formula II.

Formula II

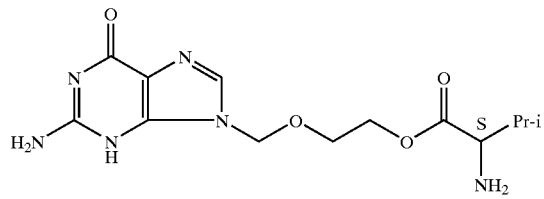

For oral administration, it is advantageous to administer valacyclovir rather than acyclovir because acyclovir is poorly absorbed from the gastrointestinal tract after oral administration in both animals and humans. In contrast, valacyclovir is rapidly absorbed from the gastrointestinal tract after oral administration. Moreover, valacyclovir is converted rapidly and virtually completely to acyclovir after oral administration in healthy adults. The conversion of valacyclovir is thought to result from first-pass intestinal and hepatic metabolism through enzymatic hydrolysis.

Acyclovir kills viruses by inhibiting viral DNA synthesis. Because acyclovir is a guanosine analog which lacks the 3'-hydroxyl on the side chain, it causes DNA chain termination during viral DNA replication. In virus infected cells, acyclovir is converted to the monophosphate derivative (acyclovir-MP) by a viral enzyme, thymidinine kinase. Acyclovir-MP is then phosphorylated to the diphosphate and triphosphate analogs by cellular enzyme. Incorporation of activated acyclovir into the primer strand during viral DNA replication, leads to chain termination, since without the 3' hydroxyl the DNA chain can not be extended. Since uninfected cells lack the viral enzyme thymidine kinase, acyclovir is selectively activated only in cells infected with viruses that code for the appropriate kinases.

U.S. Pat. No. 4,199,574 discloses the treatment of viral infections with acyclovir.

U.S. Pat. No. 4,957,924 (the '924 patent") discloses amino acid esters of the purine nucleoside acyclovir, pharmaceutically acceptable salts thereof and their use in the treatment of herpes virus infections. Also disclosed are pharmaceutical formulations and processes for the preparation of such compounds. Valacyclovir and its salts, including the hydrochloride salt, are among the disclosed compounds.

The '924 patent further discloses a method for the preparation of valacyclovir by condensation of CBZ-Valine and acyclovir in Dimethylform amide (DMF) with catalytic amount of 4-dimethylaminopyridine (DMAP) and Dicyclohexylcarbodiimide (DCC) as a coupling reagent.

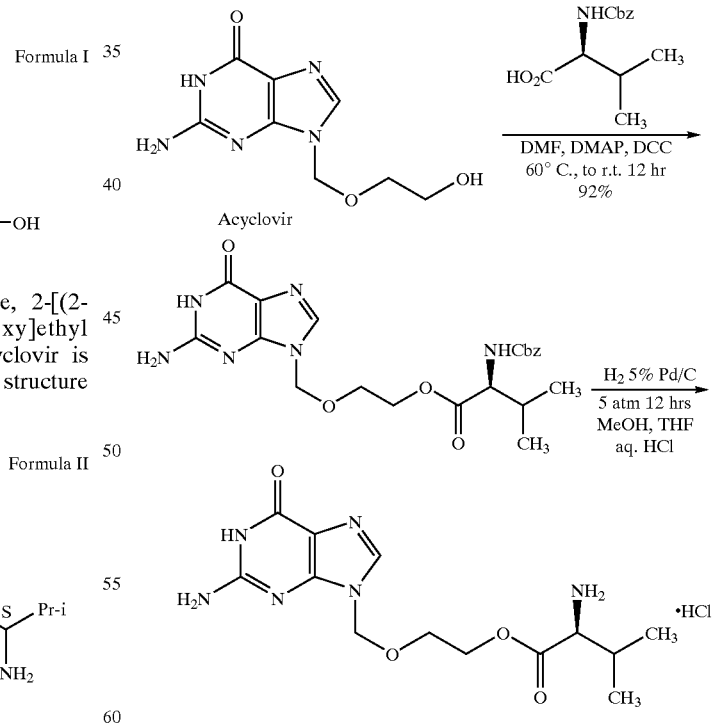

U.S. Pat. No. 6,107,302, incorporated herein by reference, discloses an anhydrous crystalline form of valacyclovir hydrochloride and a process of preparation.

The discovery of a new crystalline form of a pharmaceutically useful compound provides an opportunity to improve the performance characteristics of a pharmaceutical product.

It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new crystalline forms of a useful compound. For a general review of polymorphs and the pharmaceutical applications of polymorphs see G. M. Wall, *Pharm. Manuf.* 3, 33 (1986); J. K. Haleblian and W. McCrone, *J. Pharm. Sci.,* 58, 911 (1969); and J. K. Haleblian, *J. Pharm. Sci.,* 64, 1269 (1975), all of which are incorporated herein by reference.

The solid state physical properties of crystalline forms of a pharmaceutically useful hydrochloride can be influenced by controlling the conditions under which the hydrochloride salt is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular crystalline form of a substance. The crystalline form may give rise to thermal behavior different from that of the amorphous material or another crystalline form. Thermal behavior is measured in the laboratory by such techniques as capillary melting point, thermogravimetric analysis (TGA) and differential scanning calorimetry (DSC) and can be used to distinguish some crystalline forms from others. A particular crystalline form may also give rise to distinct spectroscopic properties that may be detectable by powder X-ray crystallography, solid state $^{13}$C NMR spectrometry and infrared spectrometry.

SUMMARY OF THE INVENTION

In one aspect, the present invention relates to valacyclovir hydrochloride in crystalline forms I, II, IV, V, VI, and VII as well as admixtures of two or more of these forms.

In another aspect, the present invention relates to methods of making forms I, II, III, IV, V, VI and VII and mixtures thereof. The present invention also relates to pharmaceutical compositions containing valacyclovir hydrochloride in crystalline forms I, II, IV, V, VI, and VII as well as mixtures of two or more of these.

In one aspect, the present invention relates to valacyclovir hydrochloride in form I, characterized by x-ray diffraction peaks (reflections) at about 3.7, 8.6, 10.6, 10.9, 16.5, 24.0, and 27.2±0.2 degrees two-theta.

In one aspect, the present invention relates to valacyclovir hydrochloride in form I, characterized by x-ray diffraction peaks (reflections) at about 3.7, 8.6, 10.6, 10.9, 16.5, 24.0, and 27.2±0.2 degrees two-theta, and further characterized by x-ray diffraction peaks (reflections) at 9.5, 13.3, 20.1, 21.4, and 26.7 degrees two theta.

Figure 1:
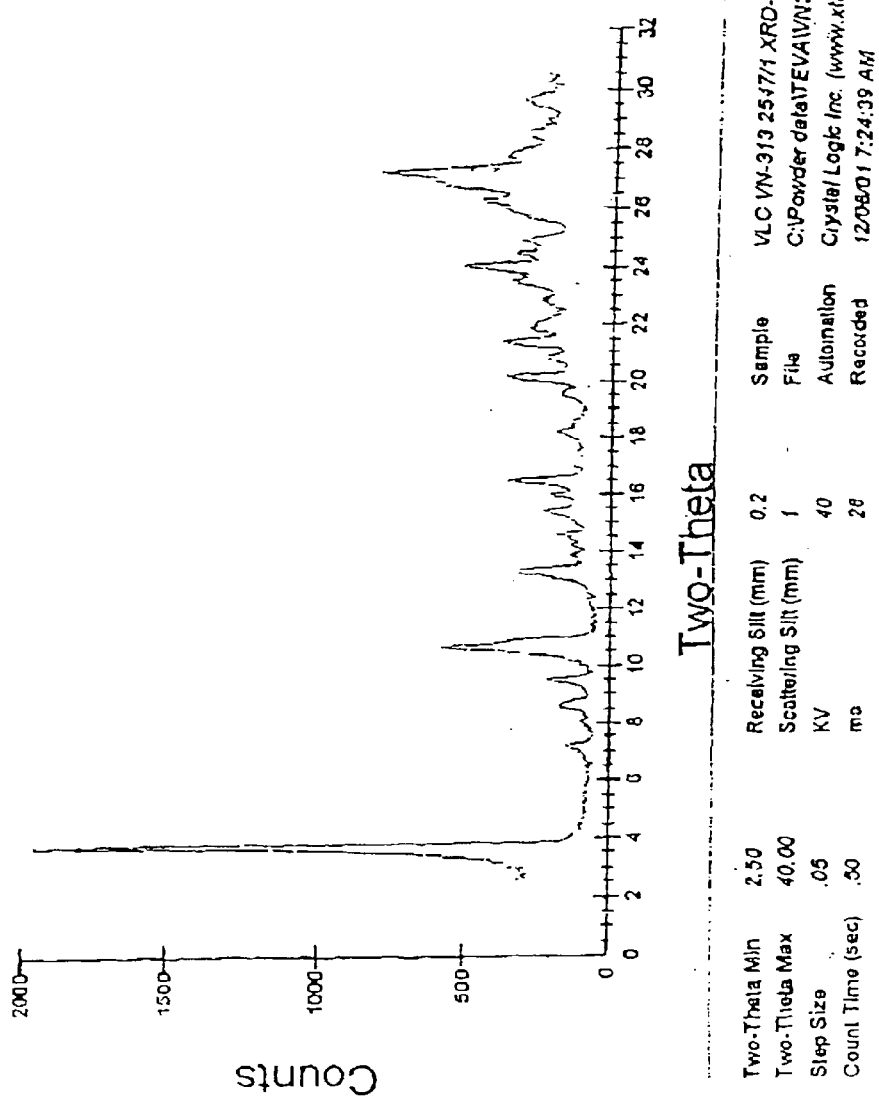
FIG. 1 shows a representative X-ray diffraction pattern of valacyclovir hydrochloride in form I.

In another aspect, the present invention also relates to valacyclovir hydrochloride in form I having the x-ray powder diffraction pattern substantially as shown in FIG. 1.

In another aspect, the present invention also relates to valacyclovir hydrochloride in form I further characterized as having a weight loss of between about 6% and about 9% as measured by thermogravimetric analysis over the temperature range between about 25° C. and about 140° C. This water content corresponds to the stochiometric amount of water in the sesquihydrate and is agreement with water contend determined by Karl-Fisher.

The present invention also relates to a pharmaceutical composition including valacyclovir hydrochloride in form I.

In another aspect, the present invention also relates to valacyclovir hydrochloride in form II.

The present invention also relates to valacyclovir hydrochloride in form II, characterized by x-ray diffraction peaks (reflections) at about 6.6, 11.5, 17.2, 19.0, 21.5, 27.4 and 28.0±0.2 degrees two-theta.

In another aspect, the present invention also relates to valacyclovir hydrochloride in form II, characterized by x-ray diffraction peaks (reflections) at about 6.6, 11.5, 17.2, 19.0, 21.5, 27.4 and 28.0±0.2 degrees two-theta, and further characterized by additional x-ray diffraction peaks (reflections) at 9.2, 15.6, and 26.3±0.2 degrees two-theta.

The present invention also relates to valacyclovir hydrochloride in form II, further characterized as having an endothermic peak at about 211° C. through differential thermal analysis.

Figure 3:
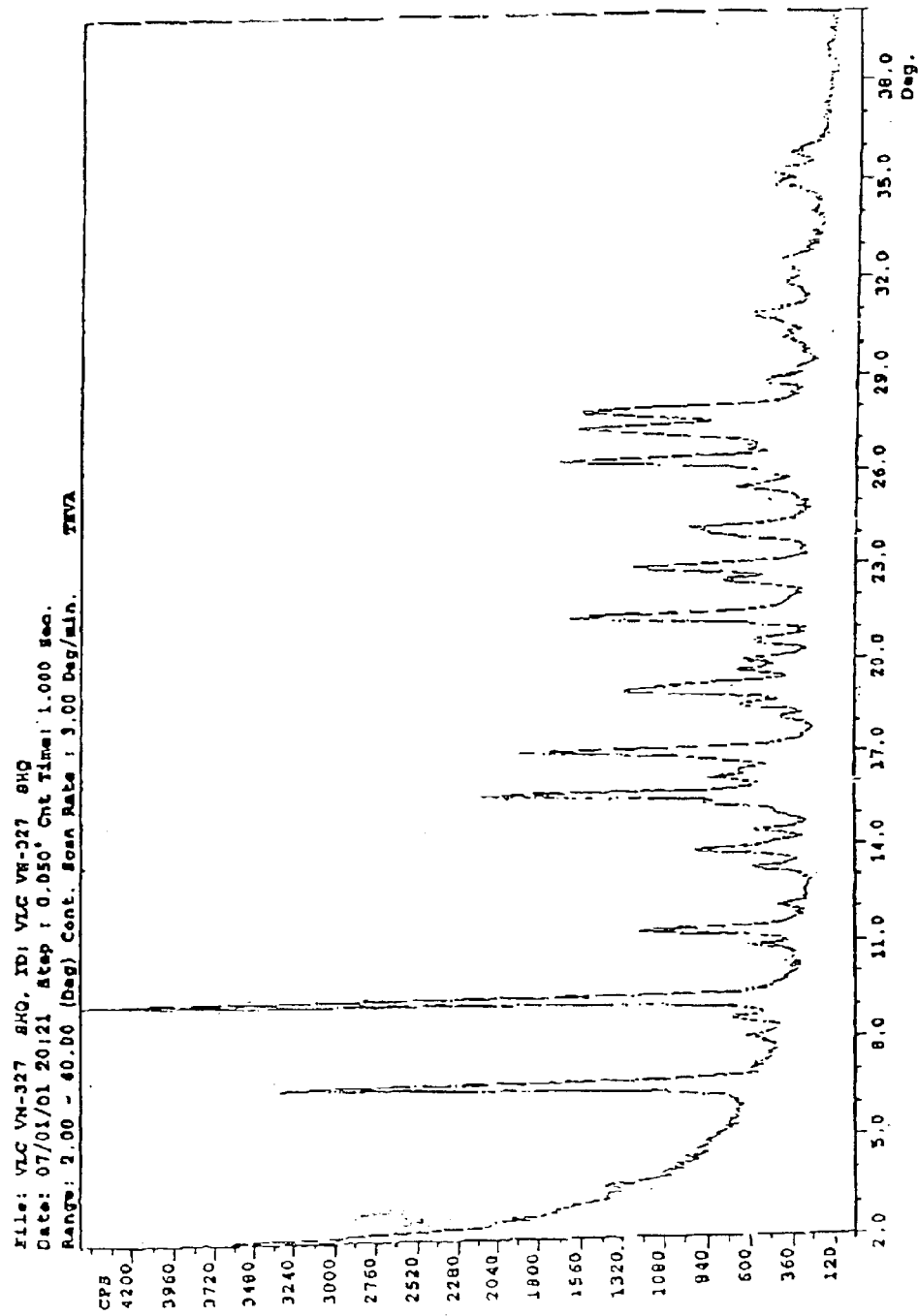
FIG. 3 shows a representative X-ray diffraction pattern of valacyclovir hydrochloride in form II.

The present invention also relates to valacyclovir hydrochloride in form II having the X-ray powder diffraction pattern substantially as shown in FIG. 3.

The present invention also relates to a pharmaceutical composition including valacyclovir hydrochloride form II.

In another aspect, the present invention relates to valacyclovir hydrochloride form IV.

In yet another aspect, the present invention relates to valacyclovir hydrochloride form IV, characterized by x-ray diffraction peaks at about 3.6, 10.7, 15.1, 26.9, and 28.1±0.2 degrees two-theta.

In yet another aspect, the present invention relates to valacyclovir hydrochloride form IV, characterized by x-ray diffraction peaks at about 3.6, 10.7, 15.1, 26.9, and 28.1±0.2 degrees two-theta, and further characterized by x-ray diffraction peaks (reflections) at 7.2, 8.7, 9.5, 13.3, 16.5, 23.5, and 24.0 degrees two-theta.

In another aspect, the present invention relates to valacyclovir hydrochloride in form IV further characterized by additional x-ray diffraction reflections at about 7.2°, 8.6°, 9.5°, 13.3°, 15.2°, 27.3°, and 28.1°±0.2° two-theta.

Figure 6:
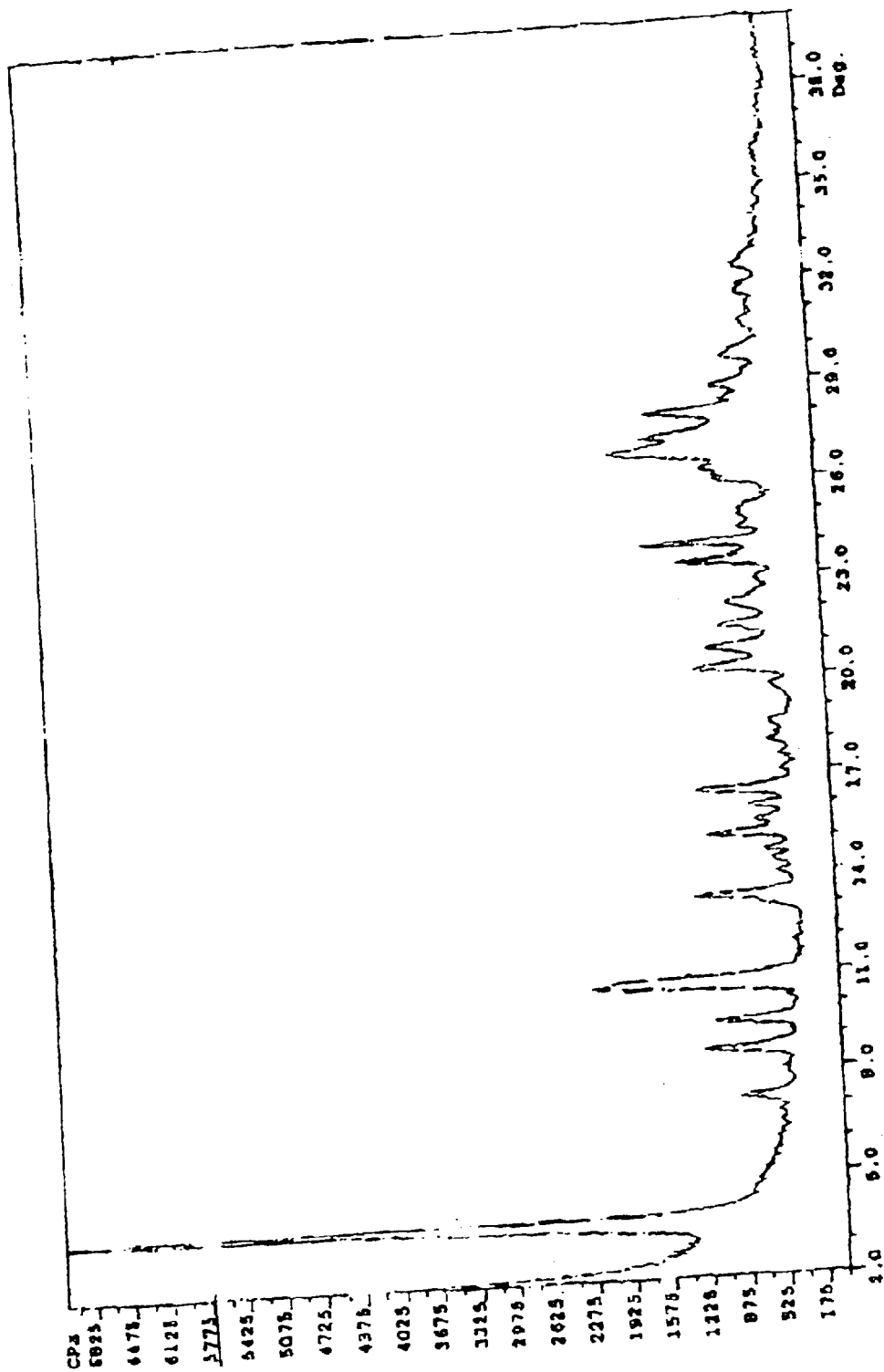
FIG. 6 shows a representative X-ray diffraction pattern obtained when valacyclovir hydrochloride was incubated in controlled humidity cell having a relative humidity of 100% for 1 week to yield valacyclovir hydrochloride in form IV.
Figure 7:
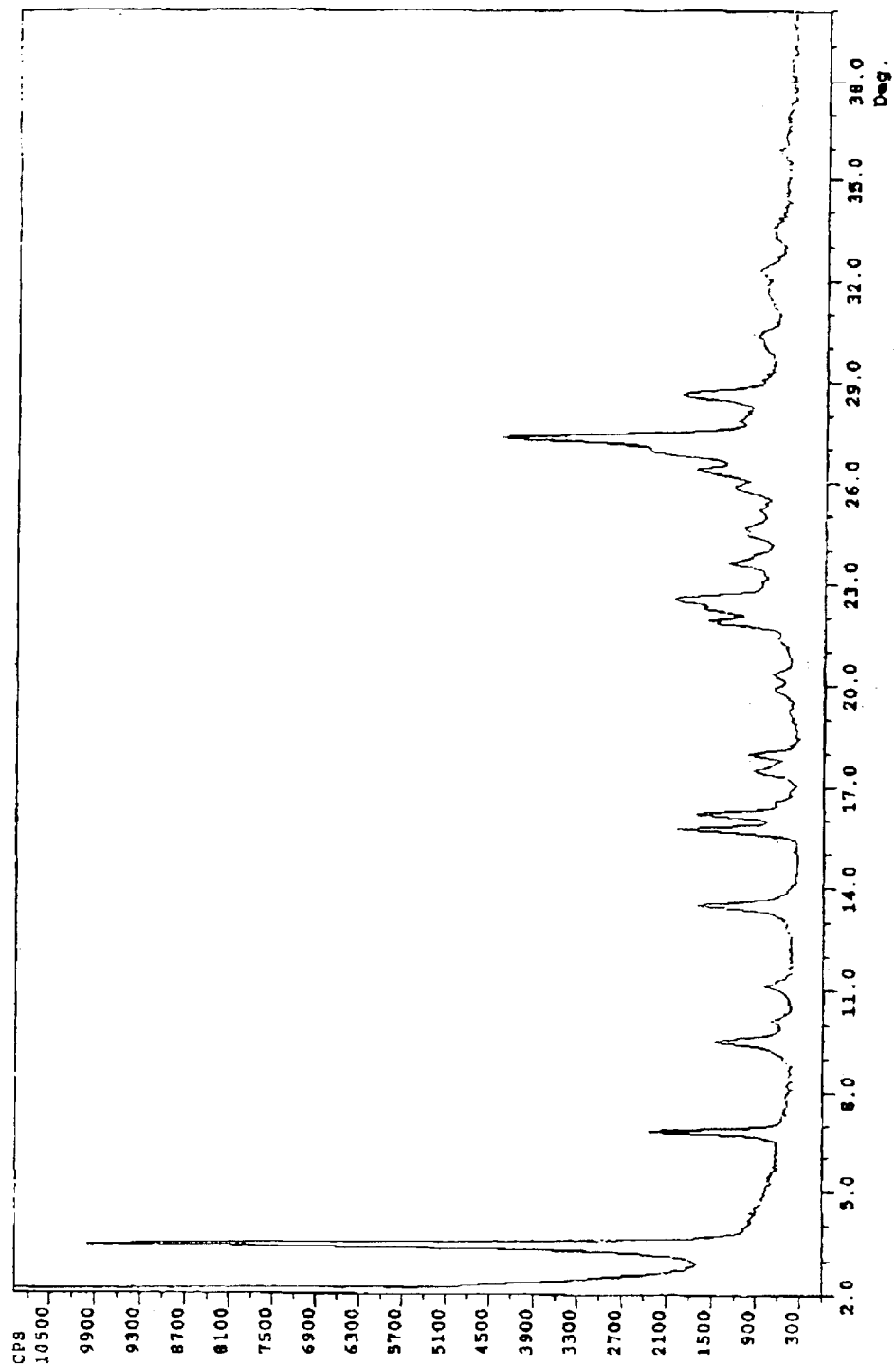
FIG. 7 shows a representative x-ray diffraction diagram for valacyclovir hydrochloride in form V.
Figure 8:
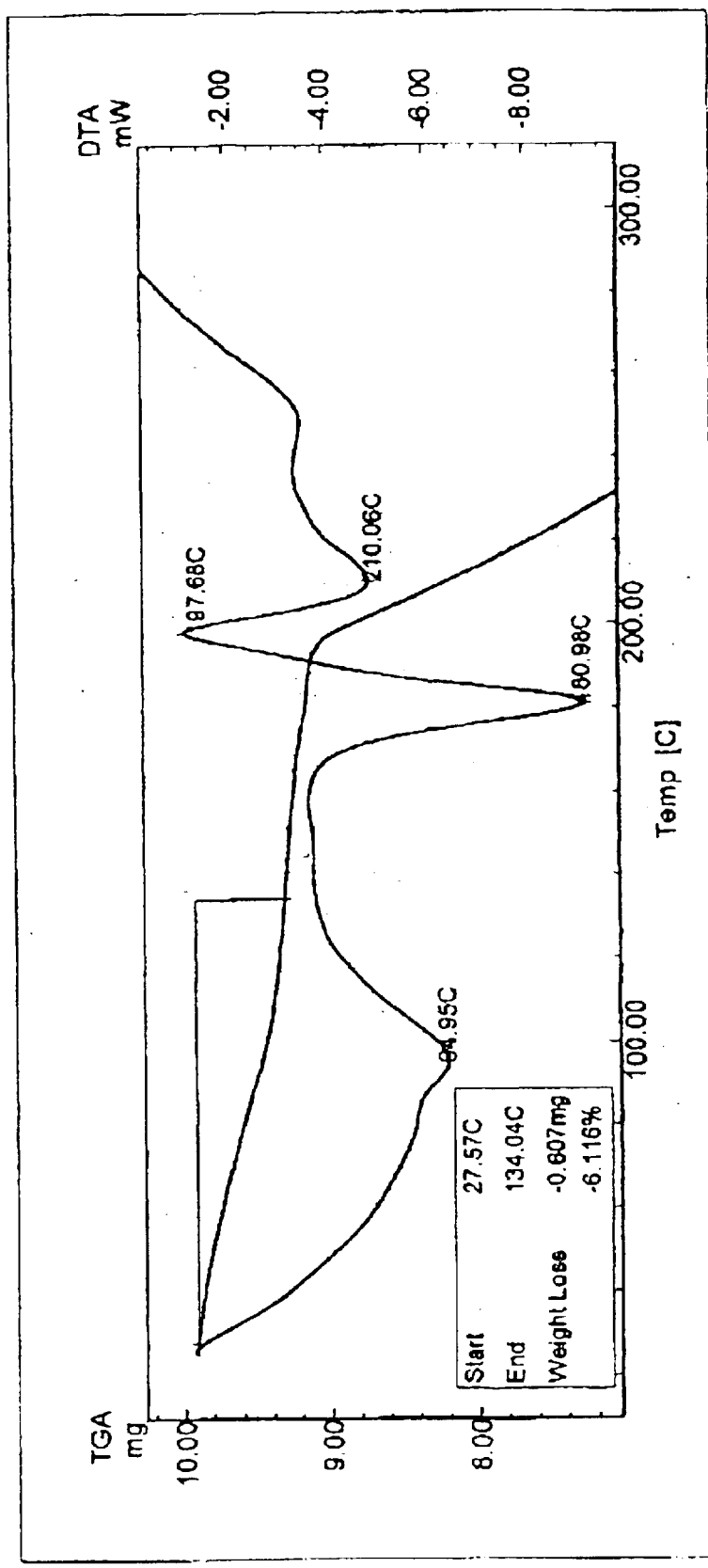
FIG. 8 shows representative differential thermal analysis and thermogravimetric thermograms for valacyclovir hydrochloride in form V.
Figure 9:
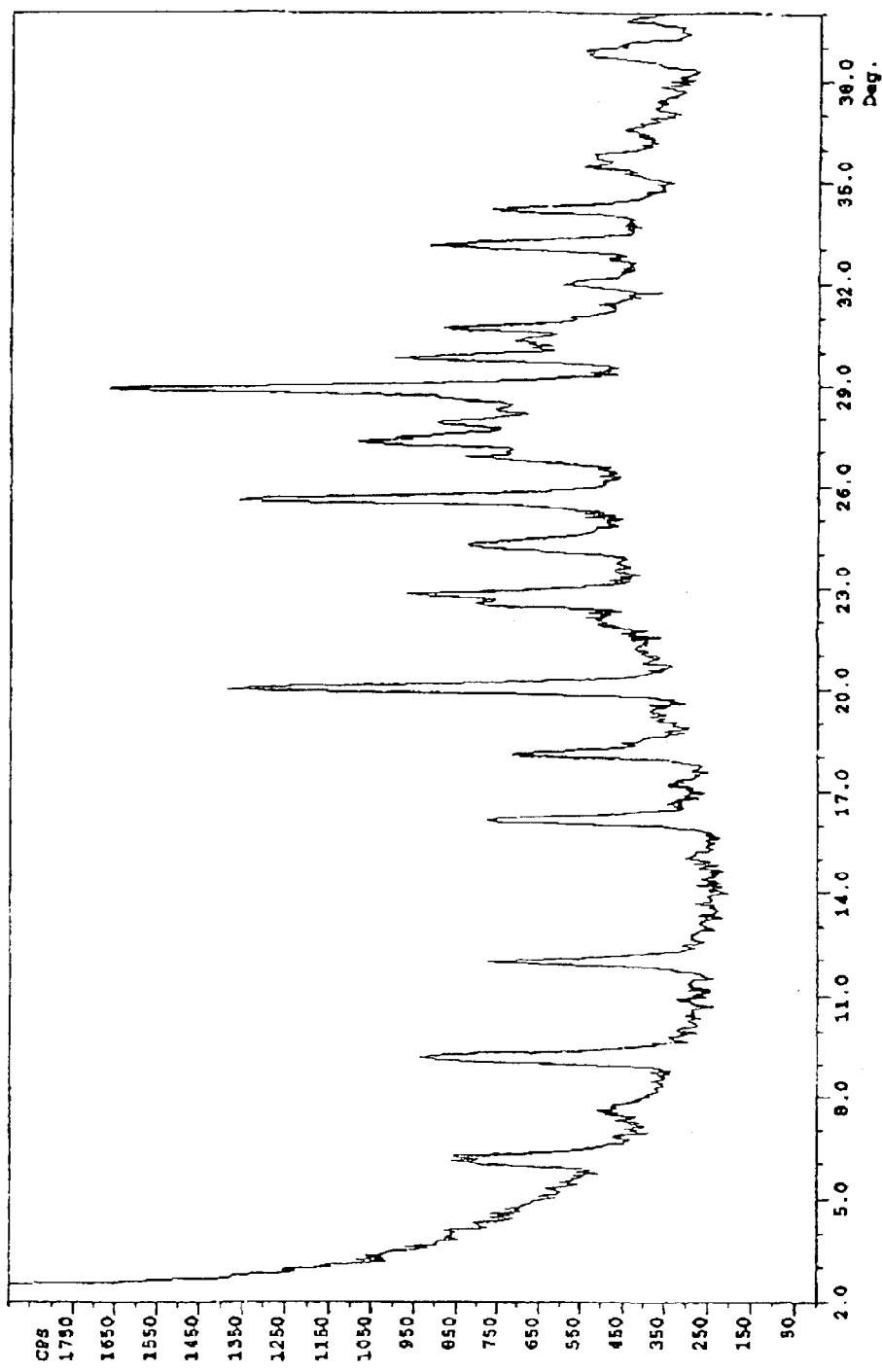
FIG. 9 shows a representative X-ray diffraction pattern for valacyclovir hydrochloride in form VI.
Figure 10:
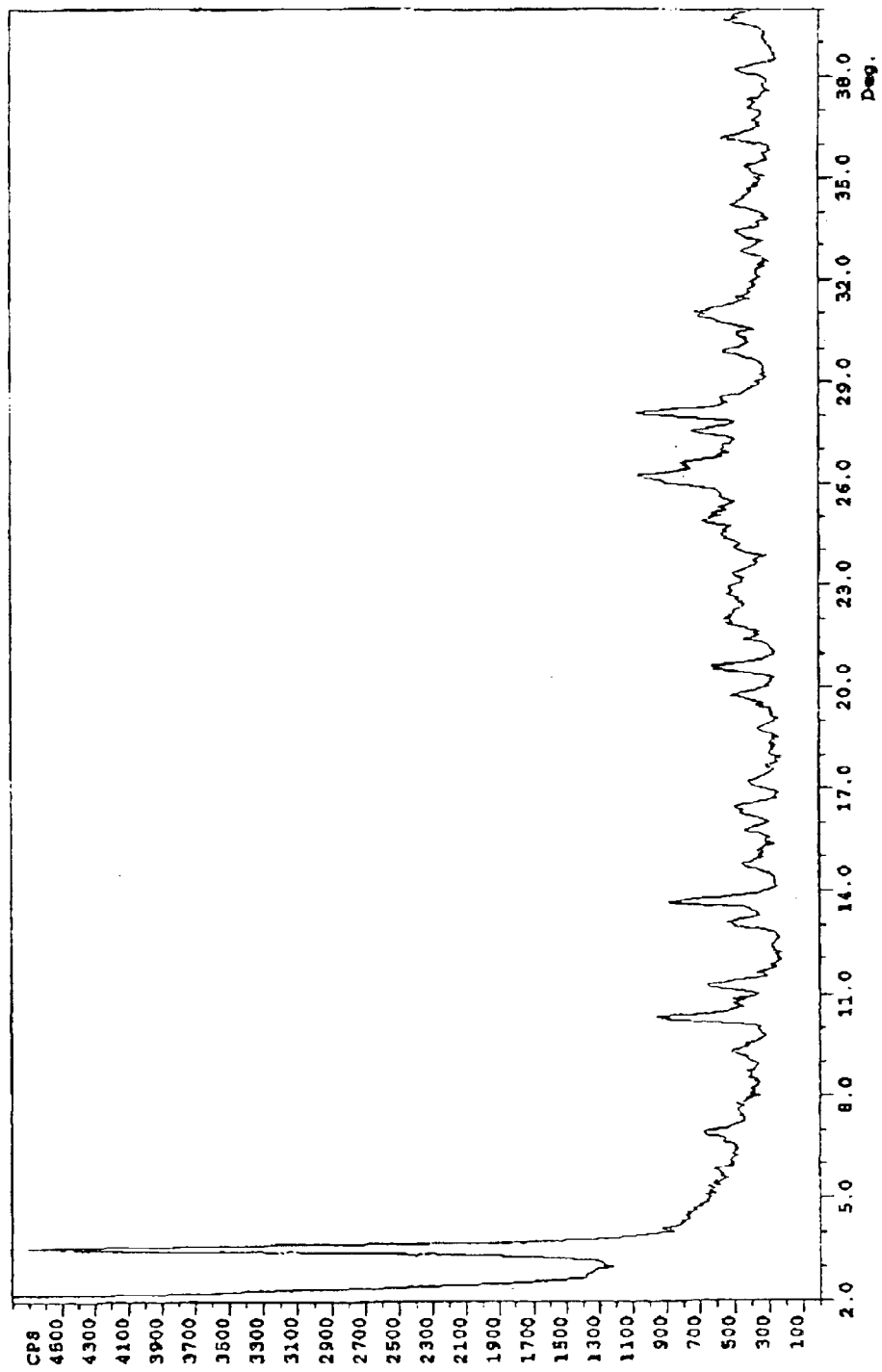
FIG. 10 shows a representative X-ray diffraction pattern for valacyclovir hydrochloride in form VII.

The present invention also relates to valacyclovir hydrochloride form IV having the X-ray powder diffraction pattern substantially as shown in FIG. 6

In another aspect, the present invention relates to valacyclovir hydrochloride form IV further characterized as having a weight loss of between about 9% and about 11% as measured by thermogravimetric analysis over the temperature range between about 25° C. and about 170° C. This LOD value corresponds to the stoichiometric amount of water determined by the Karl-Fisher method.

The present invention also relates to a pharmaceutical composition including valacyclovir hydrochloride form IV.

In one aspect, the present invention relates to valacyclovir hydrochloride in crystalline form V.

In another aspect, the present invention also relates to valacyclovir hydrochloride in form V having the X-ray powder diffraction pattern substantially as shown in FIG. 12.

In another aspect, the present invention relates to valacyclovir hydrochloride in form V having x-ray reflections (peaks) at about 6.7°, 15.7°, 16.2°, and 22.60°±10.2° 2θ.

In another aspect, the present invention relates to valacyclovir hydrochloride in form V having additional x-ray reflections (peaks) at about 3.4°, 9.5°, 13.5°, 21.9°, 27.2°, and 28.6°±0.2° 2θ.

In another aspect, the present invention relates to valacyclovir hydrochloride in form V further characterized as having a weight loss of between about 5% and about 7% as measured by thermogravimetric analysis over the temperature range between about 25° C. and about 130° C.

In another aspect, the present invention relates to valacyclovir hydrochloride in form V further characterized by a broad endothermic peak at about 95° C. and a sharp endothermic peak at about 180° C. as exhibited by differential thermogravimetric analysis.

The present invention also relates to pharmaceutical compositions including valacyclovir hydrochloride in form V.

In yet another aspect, the present invention relates to valacyclovir hydrochloride in crystalline in form VI.

In another aspect, the present invention relates to valacyclovir hydrochloride in form VI characterized by x-ray diffraction peaks (reflections) at about 6.2°, 9.2°, 12.1°, 20.2° and 25.7°±0.2° 2θ.

In another aspect, the present invention relates to valacyclovir hydrochloride in form VI characterized by the x-ray powder diffraction pattern substantially as shown in FIG. 14.

The present invention also relates to pharmaceutical compositions including valacyclovir hydrochloride in form VI.

In another aspect, the present invention relates to valacyclovir hydrochloride in crystalline form VII.

In still another aspect, the present invention relates to valacyclovir hydrochloride in form VII characterized by an X-ray diffraction pattern having peaks (reflections) at about 3.5°, 10.3°, 13.6°, 26.2° and 28.1° 2θ.

In still another aspect, the present invention relates to valacyclovir hydrochloride in form VII characterized by the x-ray powder diffraction pattern substantially as shown in FIG. 15.

The present invention also relates to pharmaceutical compositions including valacyclovir hydrochloride in form VII.

In another aspect, the present invention also relates to a process for preparing valacyclovir hydrochloride form I, including the step of suspending valacyclovir hydrochloride as a slurry in a slurry solvent, wherein the slurry solvent is selected from the group that is ethyl acetate, acetone, methyl ethyl ketone, dioxane, methylene chloride, t-butyl methyl ether, and tetrahydrofurane.

In another aspect, the present invention also relates to a process for preparing valacyclovir hydrochloride in form I, including the steps of suspending valacyclovir hydrochloride as a slurry in a slurry solvent, wherein the slurry solvent is selected from the group that is ethyl acetate, acetone, methyl ethyl ketone, dioxane, methylene chloride, t-butyl methyl ether, and tetrahydrofurane; isolating valacyclovir hydrochloride in form I from the slurry; and drying valacyclovir form I at a temperature between about 20° C. and about 70° C.

In another aspect, the present invention relates to a method of making valacyclovir hydrochloride in form II including the step of slurrying, at ambient temperature, valacyclovir hydrochloride in a slurry solvent selected from isopropyl alcohol, 1-butanol, or ethanol.

In another aspect, the present invention relates to a method of making valacyclovir hydrochloride in form II including the step of slurrying valacyclovir hydrochloride in toluene and, optionally, isolating valacyclovir hydrochloride in form II from the slurry and drying the valacyclovir hydrochloride form II, preferably at a temperature of about 60° C. Optionally, drying is at a pressure less than about 500 mm Hg and a temperature of about 50° C.

In yet another aspect, the present invention relates to a reflux slurry method of making valacyclovir hydrochloride in form II including the steps of slurrying valacyclovir in a slurry solvent selected from acetonitrille, methyl ethyl ketone, ethyl acetate, acetone, and toluene, heating the slurry to reflux, refluxing the resulting mixture, and isolating valacyclovir hydrochloride in form II from the mixture.

In another aspect, the present invention relates to a method of making valacyclovir hydrochloride in form II including the steps of slurrying valacyclovir hydrochloride in toluene; heating the slurry to reflux; adding methanol to the slurry; refluxing the resulting mixture; and isolating valacyclovir hydrochloride in form II from the mixture.

In another aspect, the present invention relates to a method of making valacyclovir hydrochloride in form III including the step of incubating valacyclovir hydrochloride in an atmosphere saturated with vapors of at least one of the following incubating solvents: isopropanol, ethanol, butanol, acetone, ethyl acetate, tetrahydrofurane, acetonitrile, methanol, and water. The valacyclovir hydrochloride can be in solid form or in solution in the incubating solvent.

In another aspect, the present invention relates to a method of making valacyclovir in form IV including the step of incubating valacyclovir hydrochloride in an atmosphere having a relative humidity of about 100%.

In another aspect, the present invention relates to a method of making valacyclovir hydrochloride in form V including the step of mixing a solution of valacyclovir hydrochloride in water with a lower aliphatic alcohol.

In another aspect, the present invention relates to a method of making valacyclovir hydrochloride in form V including the step of mixing a solution of valacyclovir hydrochloride in water with iso-propanol.

In another aspect, the present invention relates to a method of making valacyclovir hydrochloride in form VI including the step of mixing a solution of valacyclovir hydrochloride in a first solvent including water and an aliphatic monocarboxylic acid with a second solvent including a water-miscible ketone, particularly acetone, to form a suspension.

In another aspect, the present invention relates to a method of making valacyclovir hydrochloride in form VI including the step of mixing a solution of valacyclovir hydrochloride in a first solvent including between about 30% and about 60% by volume of water, the remainder an aliphatic monocarboxylic acid, with a second solvent including a water-miscible ketone in an amount that is about 2 to about 5 times the volume of the first solvent.

In another aspect, the present invention relates to a method of making valacyclovir hydrochloride in form VI including the step of filtering the solution of valacyclovir hydrochloride in a first solvent including water and an aliphatic monocarboxylic acid; then mixing the solution with a second solvent including a water-miscible ketone, preferably acetone, to form a suspension; and optionally, agitating the suspension at a temperature less than about −10° C. and isolating valacyclovir hydrochloride in form VI from the suspension.

In another aspect, the present invention relates to a method of making valacyclovir hydrochloride in form VII including the step of mixing a solution of valacyclovir hydrochloride in a first solvent that is essentially water with a second solvent that includes a water-miscible ketone, preferably acetone, to form a suspension; and optionally further including the steps of agitating the suspension at a temperature less than about 10° C. and isolating valacyclovir hydrochloride in form VII from the suspension. A method of making valacyclovir hydrochloride in form I including the step of heating valacyclovir hydrochloride for about 2 hours at a temperature between about 10° C. and about 130° C.

In another aspect, the present invention relates to a method of making valacyclovir hydrochloride in form I including the steps of dissolving valacyclovir hydrochloride in a solvent, and evaporating the solution at a reduced pressure. Preferably, the solvent is a polar organic solvent having 4 or fewer carbon atoms. Most preferably, the solvent is an alcohol, preferably methanol.

In another aspect, the present invention relates to a pharmaceutical composition including any one of valacyclovir hydrochloride in form I, II, IV, V, VI or VII.

In another aspect, the present invention relates to a pharmaceutical composition including any mixture of two or more of valacyclovir hydrochloride in form I, II, IV, V, VI or VII.

DETAILED DESCRIPTION OF THE INVENTION

The present invention provides valacyclovir hydrochloride in new crystalline forms I, II, IV, V, VI, and VII as well as admixtures of two or more of these forms. The present invention also provides methods for preparing valacyclovir hydrochloride in crystalline forms I, II, III, IV, V, VI, and VII as well as admixtures of two or more of these forms.

The present invention further relates to the solid state physical properties of these crystalline forms of valacyclovir hydrochloride as prepared by any of the methods of the present invention, as well as by other methods known to those skilled in the art.

As used herein, unless the context requires otherwise, the term "valacyclovir hydrochloride" includes anhydrous forms, hydrates, solvates, and all crystalline forms (both polymorphs and pseudopolymorphs), of valacyclovir hydrochloride. As used herein, the term polymorphs is used broadly to include both polymorphs and pseudopolymorphs, i.e., all crystalline forms.

As used herein in connection with a measured quantity, the term "about" refers to that variation in the measured quantity as would be expected by the skilled artisan performing the measurement and exercising a level of care commensurate with the objective of the measurement and the precision of the measuring apparatus being used.

For the purposes of this specification, ambient or room temperature is from about 20° C. to about 25° C., elevated temperature means above about 38° C., and cold temperature means below about −10° C.

All powder x-ray diffraction patterns were obtained by methods known in the art using a Scintag X'TRA X-ray powder diffractometer, equipped with a solid state Si(Li) detector thermoelectrically cooled, at scanning speed of 3° min.$^{-1}$. The scanning range was 2–40 degrees two-theta. Copper radiation of □=1.5418° was used. The term x-ray diffraction "peaks" as used herein refers to x-ray diffraction "reflections" measured using an x-ray powder diffractometer. "Wet" samples (i.e. samples not dried) was analyzed as is. Dry samples were gently ground before analysis.

The differential thermal analysis ("DTA") and thermogravimetric analysis ("TGA") curves presented herein were obtained by methods known in the art using a DTG Shimadzu model DTG-50 (combined TGA and DTA). The weight of the samples was about 9 to about 13 mg. The samples were scanned up to about 300° C. at a rate of 10° C./min. Sample chambers were purged with nitrogen gas at a flow rate of 20 mL/min. Uncovered standard alumina crucibles were used.

Thermogravimetric analysis (TGA) is a measure of the thermally induced weight loss of a material. Thermogravimetric analysis (TGA) is a thermal analysis technique well known in the art that detects and measures events that have associated with them a loss of mass, e.g. loss of water of hydration, as a function of temperature.

DTA denotes differential thermal analysis, a technique well known in the art, that detects and measures thermal events in a sample, e.g. phase transitions, in which heat is either absorbed (endothermic) or liberated (exothermic).

Karl Fisher analysis, which is well known in the art, is also used to determine the quantity of water in a sample.

The term "water content" refers to the content of water based upon the Loss on Drying method (the "LOD" method) as described in U.S. Pharmacopeia Forum, Vol. 24, No. 1, p. 5438 (January–February 1998), the Karl Fisher assay for determining water content or thermogravimetric analysis (TGA). The term "equivalents of water" means molar equivalents of water. All percentages referenced herein are by weight unless otherwise indicated.

Those skilled in the art will also understand that the term "anhydrous" when used in reference to valacyclovir hydrochloride describes valacyclovir hydrochloride which is substantially free of water. Those skilled in the art will appreciate that the term "hydrate" when used in reference to valacyclovir hydrochloride describes a crystalline material having a water content of about 6–10% w/w.

When used in describing purity, percent refers to area percent determined by high-pressure liquid chromatography (HPLC), a method well-known to those skilled in the art, and is calculated according to the equation:

% impuruty $i$=100×(area under peak $i$)/($\Sigma$ area of all peaks).

In one embodiment, the present invention provides valacyclovir hydrochloride in form I ("Form I").

Valacyclovir hydrochloride in form I is characterized by an x-ray diffraction pattern with peaks (reflections) at about 3.7, 8.6, 10.6, a0.9, 13.3, 16.5, 24.0, and 27.2±0.2 degrees two-theta. FIG. 1 shows a representative x-ray powder diffraction pattern of valacyclovir hydrochloride in form I.

Figure 2:
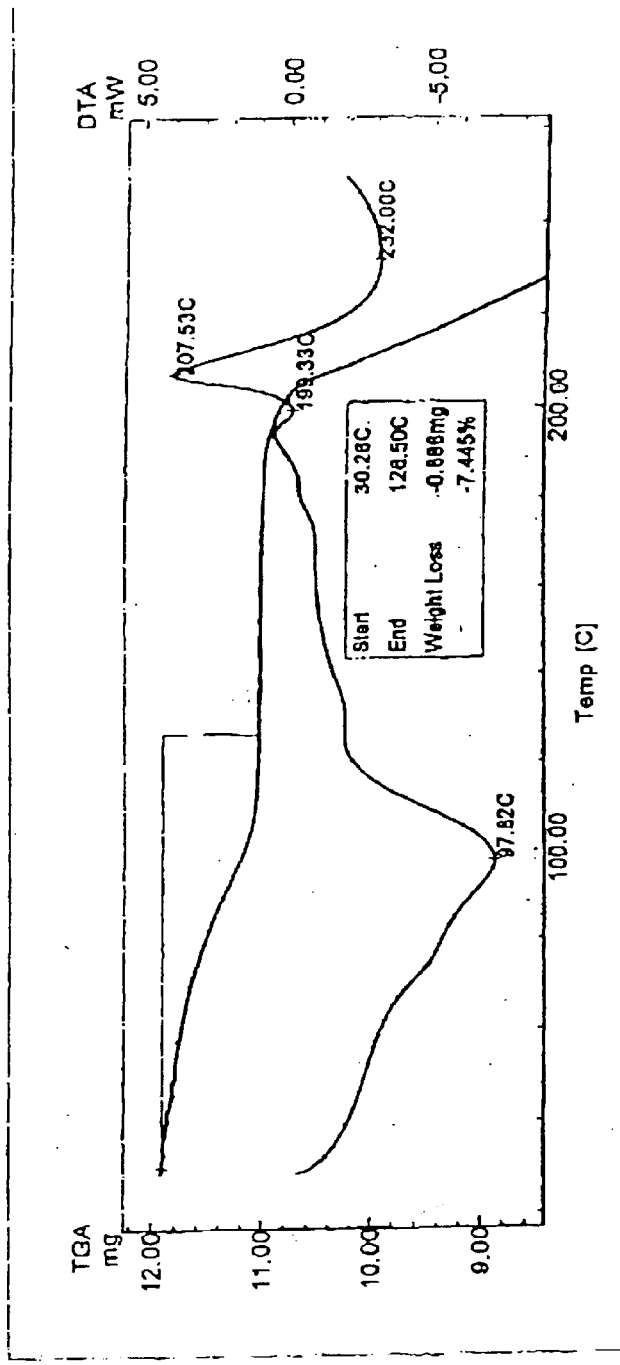
FIG. 2 shows a representative DTG thermogram of valacyclovir hydrochloride in form I.

Valacyclovir hydrochloride in form I is also characterized by the thermal profile measured using the DTG-50 as discussed above, which provides both TGA and DTA thermograms as shown in FIG. 2. The DTA thermogram shows a broad endotherm below 125° C. The weight loss curve also shows a weight loss step in this temperature range, with a measured loss on drying value from about 6% to about 9% by weight. This LOD value corresponds to the stoichiometric amount of water of valacyclovir hydrochloride sesquihydrate and agrees with the water content determined by the Karl-Fisher method.

In another embodiment, the present invention provides valacyclovir hydrochloride in form II ("Form II").

Valacyclovir hydrochloride in form II is characterized by an x-ray diffraction pattern with peaks (reflections) at about 6.6, 11.5, 17.3, 19.0, 21.5, 26.3, 27.4 and 28.0±0.2 degrees two theta. FIG. 3 shows a representative x-ray powder diffraction pattern of valacyclovir hydrochloride in form II.

Figure 4:
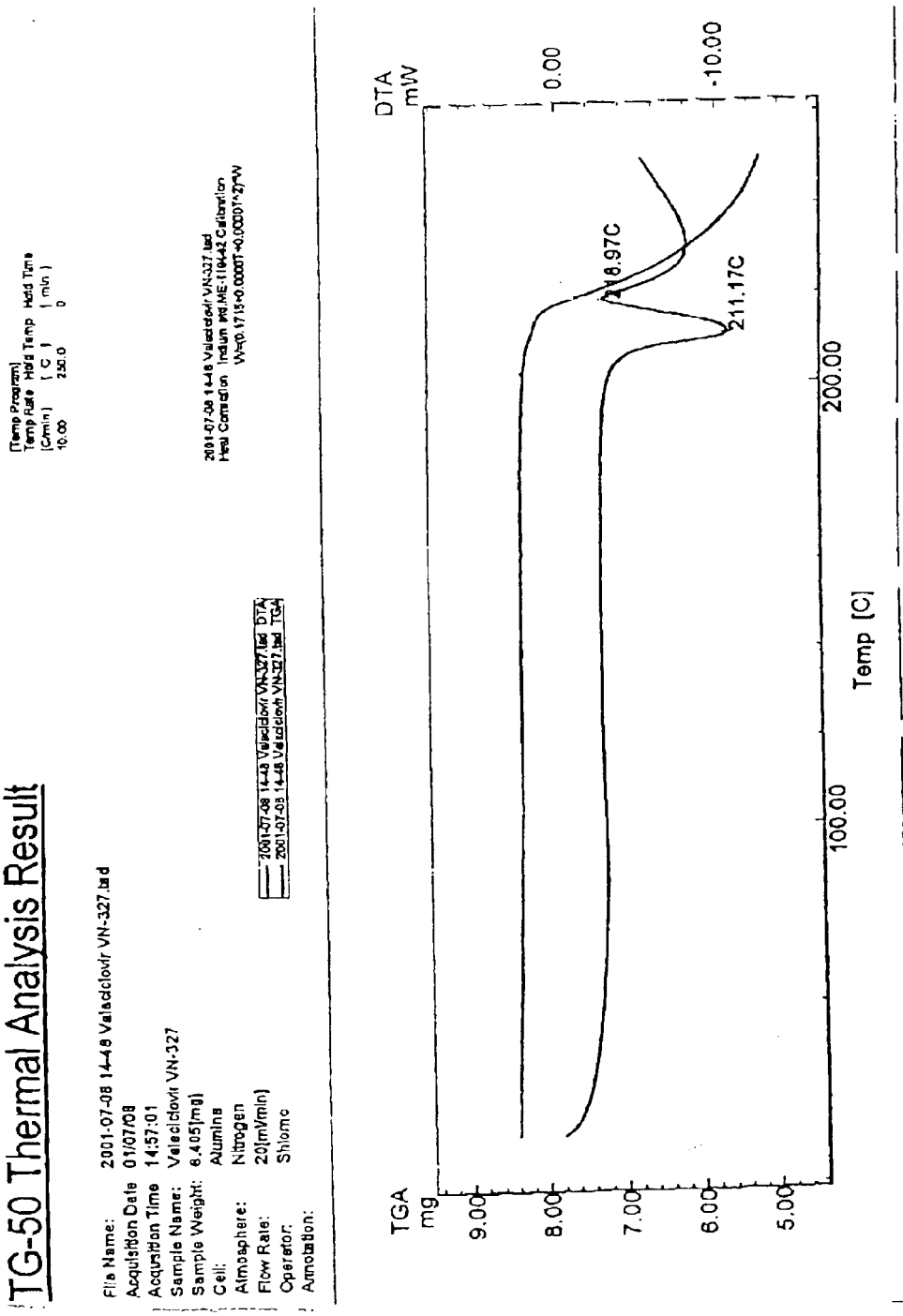
FIG. 4 shows a representative DTG thermogram of valacyclovir hydrochloride in form II.

Valacyclovir hydrochloride in form II can also be characterized by differential thermal analysis (DTA), as shown in FIG. 4, which shows an endothermic peak at 211° C. followed by an exothermic peak.

Valacyclovir hydrochloride in form III ("Form III") is the prior art anhydrous form of valacyclovir hydrochloride disclosed in U.S. Pat. No. 6,107,302.

In one embodiment, the present invention provides a method for preparing valacyclovir hydrochloride in form III.

In another embodiment, the present invention provides valacyclovir hydrochloride in form IV ("Form IV").

Valacyclovir hydrochloride in form IV is characterized by an x-ray diffraction pattern with peaks (reflections) at about 3.6, 10.7, 15.1, 26.9, and 28.1±0.2 degrees two-theta. Fig. @@ shows a representative x-ray diffraction pattern for valacyclovir hydrochloride in form IV.

Figure 5:
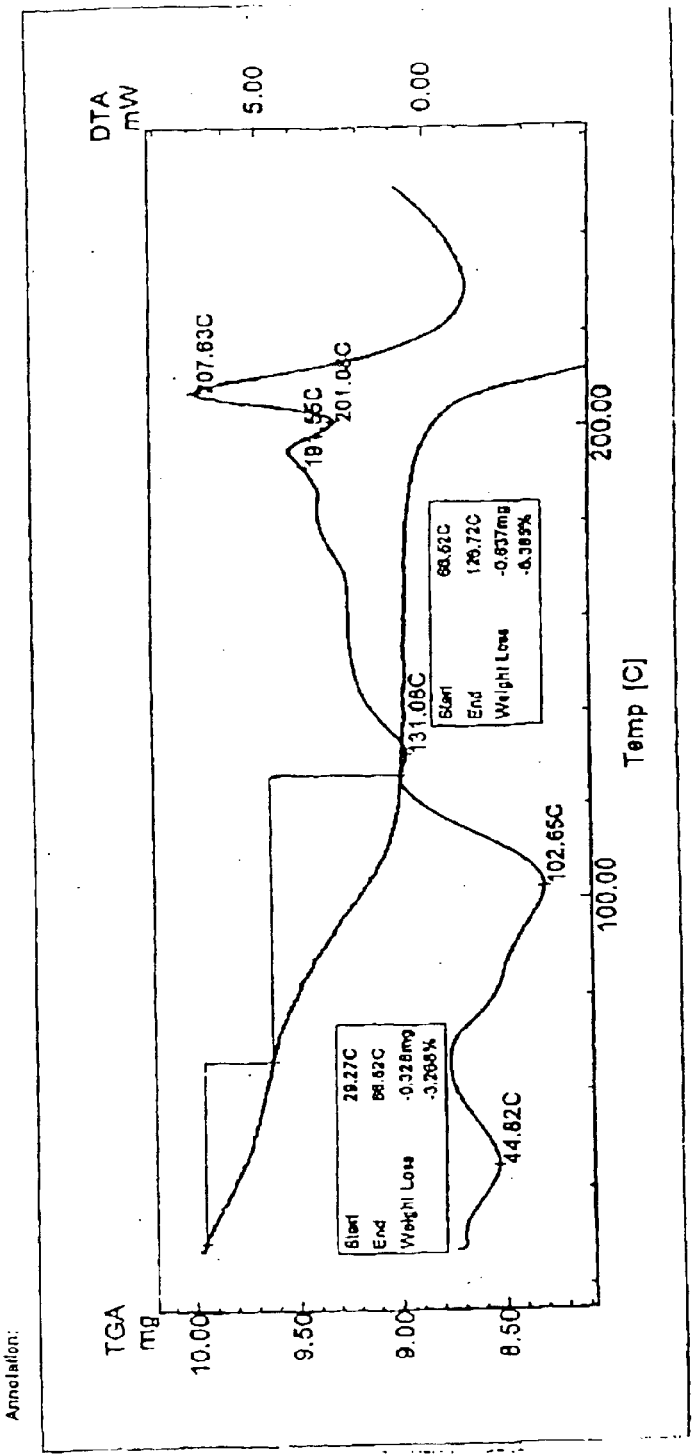
FIG. 5 shows a representative DTG thermogram of valacyclovir hydrochloride in form IV.

Valacyclovir hydrochloride in form IV can be further characterized by the thermal thermal analysis using the DTG-50 as discussed above, which provides both TGA and DTA thermograms as shown in FIG. 5. The DTA thermogram shows two broad endothermic peaks at about 45° C. and 100° C. The weight loss curve shows two weight loss steps in the temperature range of up to about 130° C. The loss on drying (LOD) value in this temperature range is about 9.7%. This corresponds to the stoichiometric amount of water of valacyclovir hydrochloride dihydrate and agrees with the water content determined by the Karl-Fisher method.

Form IV can include higher amounts of solvents, up to about 15%.

In still another embodiment, the present invention provides valacyclovir hydrochloride in form V.

Valacyclovir hydrochloride in form V is characterized by x-ray reflections (peaks) at about 6.7°, 15.7°, 16.2°, and 22.6°±0.2 degrees two-theta.

Valacyclovir hydrochloride in form V of the present invention can be further characterized by additional x-ray reflections (peaks) at about 3.4°, 9.5°, 13.5°, 21.9°, 27.2°, and 28.6°±0.2° two-theta. FIG. 12 shows a representative x-ray powder diffraction pattern of valacyclovir hydrochloride in form V.

Valacyclovir hydrochloride in form V can be further characterized by DTA and TGA measurements as shown in FIG. 13. DTA thermograms of valacyclovir hydrochloride in form V of the present invention exhibit a broad endothermic peak at about 95° C. and a sharp endothermic peak at about 180° C. The weight loss curve (TGA) shows a weight loss of between about 5% and about 7% over the temperature range between about 25° C. and about 130° C.

In another embodiment, the present invention provides valacyclovir hydrochloride in form VI ("Form VI").

Valacyclovir hydrochloride in form VI is characterized by X-ray diffraction reflections (peaks) at about 6.2°, 9.2°, 12.1°, 20.2° and 25.7°±0.2° 2θ. FIG. 14 shows a representative x-ray powder diffraction pattern for valacyclovir hydrochloride in form VI.

In yet another embodiment, the present invention provides valacyclovir hydrochloride in form VII ("Form VII").

Valacyclovir hydrochloride in form VII is characterized by x-ray reflections (peaks) at about 3.5°, 10.3°, 13.6°, 26.2° and 28.1±0.2° 2θ. FIG. 15 shows a representative x-ray powder diffraction pattern for valacyclovir hydrochloride in form VII.

The novel crystalline forms (polymorphs and pseudopolymorphs) of valacyclovir hydrochloride of the present invention can be prepared by any one or more of the methods described below, each of which represents an embodiment of the present invention. Three methods used in particular embodiments are: (1) the slurry method, also known as the trituration method; (2) the vapor incubation method; and (3) the precipitation method. Also provided are thermal and evaporative methods for making valacyclovir hydrochloride in form I.

In particular embodiments, the crystalline forms of valacyclovir hydrochloride of the present invention can be made by a slurry method that includes the step of suspending, or "slurrying", a quantity of valacyclovir hydrochloride in a slurry solvent, preferably with the aid of mechanical agitation.

Examples of procedures for forming polymorphs by the slurry method are provided in examples 1 to 21. The amount of slurry solvent can vary between about 5 mL and about 15 mL, preferably between about 8 mL and about 12 mL, most preferably about 10 mL per gram of valacyclovir hydrochloride. The slurry is agitated for a time sufficient to achieve the desired transformation. Agitation may be provided by any means known to those skilled in the art, for example by using a magnetic stirrer or a propeller-type stirrer inserted into the solution. It was surprisingly found that polymorph formation by the slurry method can be more efficient when a magnetic stirrer rather than a propeller was used to promote stirring.

The extent of transformation during agitation can be monitored by, for example, removing an aliquot of the slurry, separating the solid, and analyzing the crystal form of the solid by, for example, x-ray diffraction.

Valacyclovir hydrochloride in the resulting crystalline form can be isolated from the slurry by any means known in the art. For example, filtration (gravity or suction) or centrifugation may be used, to mention just two.

If desired, or if required to make a particular polymorph, the product isolated from the slurry method can be dried at atmospheric pressure, or it can be dried at reduced pressure.

In other embodiments, the crystal forms of the present invention can be made by a vapor incubation method. In the vapor incubation method, valacyclovir hydrochloride is exposed to an atmosphere saturated or nearly saturated with vapors of an incubating solvent. Valacyclovir hydrochloride can be exposed as solid particles, preferably in a thin layer to maximize the surface exposed to vapors of the incubating solvent, or it can be exposed as its solution in the incubating solvent. Vapor incubation can be performed by placing a quantity of a solid form of valacyclovir hydrochloride in a small open container or by incubating valacyclovir hydrochloride in a solvent atmosphere in a closed container.

Preferably, the sample is incubated for a time ranging from about 7 to about 32 days. When the incubating solvent is water, the degree of chamber humidity may be regulated using salts or salt solutions such as potassium sulphate, zinc nitrate, potassium acetate, ammonium sulphate, as is known in the art.

If desired, of if required to make a particular polymorph, product from the incubation method can be dried at atmospheric pressure, or it can be dried at reduced pressure.

Examples of procedures for preparing crystalline forms of valacyclovir hydrochloride by the vapor incubation method are provided in examples 22–27.

In still other embodiments, the crystal forms of the present invention can be made by a precipitation method that includes the step of mixing, with mechanical agitation, a solution of valacyclovir hydrochloride in a first solvent with a second solvent to form a suspension. Preferably, valacyclovir hydrochloride is practically insoluble in the second solvent.

Examples of procedures for preparing crystalline forms of valacyclovir hydrochloride by the precipitation method are provided in examples 28 to 32.

The concentration of valacyclovir hydrochloride in first solvent can vary from between about 30 to about 65%. The ratio of the volume of second solvent to solution can vary between about 3:1 to about 15:1, relative to the volume of solution in first solvent Mechanical agitation can be provided by any means known in the art, for example magnetic stirrers or paddle-, propeller- or turbine-type stirrers, to mention just a few. The skilled artisan will know to select the means of agitation depending on, among other things, the size and geometry of the vessel being used and the viscosity of the solution and suspension.

In preferred embodiments that incorporate the precipitation method, the method includes the step of agitating the suspension for about 2 to about 24 hours at a temperature less than about −10° C.

Valacyclovir hydrochloride in the resulting crystal form can be isolated from the suspension by any means known in the art. For example, filtration (gravity or suction) or centrifugation can be used, to mention just two. After isolation, the valacyclovir hydrochloride in the resulting crystal form can be dried at atmospheric pressure or at reduced pressure (vacuum), both methods of which are known in the art.

It will be understood by those of skill in the art that other methods may also be used to produce the crystalline forms disclosed herein.

In one embodiment, the present invention provides a thermal method for making valacyclovir hydrochloride in form I including the step of heating valacyclovir hydrochloride for about 1 to about 3 hours, preferably about 2 hr, at a temperature between about 30° C. and about 60° C., preferably 40° C. Preferably, the material is dried under vacuum. The product so obtained is valacyclovir hydrochloride in form I according to x-ray diffraction analysis.

In another embodiment, the present method provides an evaporative method for making valacyclovir hydrochloride in form I. In the evaporative method, valacyclovir hydrochloride is dissolved in an amount of solvent (about 200 mL to about 300 mL, preferably about 250 mL, solvent per gram of valacyclovir hydrochloride) at 40° C. The solvent is evaporated, preferably at reduced pressure, to yield valacyclovir hydrochloride in form I. Polar organic solvents, especially alcohols, having 4 or fewer carbon atoms are preferred for use in the evaporation method. Methanol is a particularly preferred solvent for use in this method.

In yet another embodiment, the present invention provides a slurry method for making valacyclovir hydrochloride in form I, including the step of suspending valacyclovir hydrochloride as a slurry in a slurry solvent, and optionally, the further steps of isolating valacyclovir hydrochloride in form I from the slurry and drying at a temperature between about 50° C. and about 70° C. The slurry solvent for preparing valacyclovir hydrochloride in form I is a non-polar organic solvent, preferably selected from ethyl acetate, acetone, methyl ethyl ketone, dioxane, methylene chloride, t-butyl methyl ether, and tetrahydrofurane.

In another embodiment, the present invention provides a slurry method for making valacyclovir hydrochloride in form II, including the step of suspending valacyclovir hydrochloride as a slurry in a slurry solvent selected from isopropyl alcohol, 1-butanol, acetonitrile, methyl ethyl ketone, ethyl acetate, ethanol, acetone and toluene.

The slurry can be agitated with any stirrer known in the art, preferably a propeller-type stirrer, and most preferably, a magnetic stirrer. The step of suspending valacyclovir hydrochloride as a slurry is performed for about 20 to about 28, preferably about 24 hours.

In another embodiment, the present invention provides a slurry method of making valacyclovir hydrochloride in form II including the steps of suspending valacyclovir hydrochloride as a slurry in a slurry solvent at reflux; adding methanol to the slurry; refluxing the resultant mixture; and isolating valacyclovir hydrochloride in form II from the mixture.

In another embodiment, the present invention provides a slurry method for making valacyclovir hydrochloride form II, including the steps of: suspending valacyclovir hydrochloride as a slurry in a toluene at reflux; adding methanol to the slurry; further refluxing the resulting slurry in mixed solvents; and isolating valacyclovir hydrochloride in form II from the resulting slurry in mixed solvents.

Valacyclovir hydrochloride in form II can be isolated from the slurry by cooling the slurry to room temperature and collecting the crystals by any means known in the art.

In a particular embodiment, isolated crystals are dried under vacuum, i.e. at a pressure less than abut 500 mm Hg at 50° C. Alternatively, the step of drying the crystals is performed at atmospheric pressure at 60° C.

In another embodiment, the present invention provides a method for making valacyclovir hydrochloride form IV, including the steps of incubating valacyclovir hydrochloride in an atmosphere saturated with vapors of at least one of the following incubating solvents: isopropanol, ethanol, butanol, acetone, ethyl acetate, letrahydrofurane, acetonitrile, methanol, and water. The valacyclovir hydrochloride can be incubated as a solid or as a solution. Acetonitrile is a preferred incubating solvent when valacyclovir hydrochloride in solid form is used.

In a particular embodiment of the vapor incubation method, valacyclovir hydrochloride is dissolved in hot methanol and incubated in an atmosphere saturated with vapors of an incubating solvent in a closed container for from about 25 to about 40 days, preferably 32 days. The incubating solvent is preferably selected from acetone, ethyl acetate, tetrahydrofuran, ethanol, or butanol.

In another particular preferred embodiment, the present invention provides a process for preparing valacyclovir hydrochloride in form IV, including the steps of incubating valacyclovir hydrochloride in form II in an atmosphere saturated with water at 100% humidity.

In another embodiment, the present invention provides a method for making valacyclovir hydrochloride in forms I and IV by the precipitation method. Valacyclovir hydrochloride is dissolved in a first solvent, preferably about 6 mL first solvent per gram of valacyclovir hydrochloride, at about 20° C. to about 30° C., preferably about 25° C. The solution in first solvent is mixed with a second solvent, in a volume amount about 10 to about 30, preferably about 17 times the volume of first solvent. The resulting suspension is stirred for about 1 hour and filtered to recover precipitate wet cake. Optionally, the precipitate wet cake is dried in vacuo at 40° C.

Water is the preferred first solvent. Polar organic solvents, protic or aprotic, are useful as second solvents. Preferred second solvents are acetonitrile, butanol, and acetone. Optionally, the second solvent can be used to form the initial solution and precipitation of the polymorph effected by addition of first solvent.

In another embodiment, the present invention provides a method of making valacyclovir hydrochloride in form V by the precipitation method, for example, by mixing a solution of valacyclovir hydrochloride in a first solvent with a second solvent that is an alcohol, preferably isopropanol.

The solution is in a first solvent that includes water and, optionally, a water-miscible organic solvent such as acetic acid, a water-miscible ketone, or, preferably, an alcohol. When a ketone is used, acetone is the preferred ketone. When alcohol is used, isopropanol is the preferred alcohol. Preferably, water is the major constituent of the solvent. Most preferably, the first solvent is water.

Preferably, the solution in the first solvent contains one part by weight valacyclovir hydrochloride and about 2 to about 6 parts by weight solvent. The solution can be made by, for example, dissolving the desired amount of valacyclovir hydrochloride in about 2 to about 6 parts by weight solvent. The valacyclovir hydrochloride can be made by any means known in the art, or it can be generated in situ from t-butoxycarbonyl valacyclovir (t-BOC Val), in which the nitrogen of the valine residue attached to the acyclovir moiety bears a butoxycarbonyl group.

When valacyclovir hydrochloride is generated in situ in a preferred embodiment, about 3 to about 7, preferably about 5, equivalents of hydrogen chloride, dissolved in a suitable vehicle, are added, preferably slowly to maintain temperature control, to a suspension of a protected valacyclovir (e.g., t-BOC valacyclovir) in a suitable solvent mentioned above. The vehicle can be any of those solvents mentioned above. Preferably, the vehicle and solvent are both water.

After addition of the hydrogen chloride, the mixture is stirred at a temperature below about 40° C., preferably at about 20° to 25° C., until the mixture essentially becomes a solution that can be roily or turbid. The mixture is then cooled to a temperature below about 10° C., preferably at about 0° C., and mixed with an alcohol, preferably isopropanol (20 to 30 volumes based on the volume of solvent used) to form a suspension. Preferably, the suspension is stirred for at least about one-half hour at this temperature. The suspension can be stirred at a temperature below about 4° C. for a period of time, for example about 8 to about 18 hours.

Valacyclovir hydrochloride in form V can be isolated from the suspension by any means known in the art. For example, isolation can be by filtration (gravity or suction) or by centrifugation, to mention just two.

Typically, valacyclovir hydrochloride in form V prepared as described above will have a chemical purity of at least about 97%.

In another embodiment, the present invention also provides a method of making valacyclovir hydrochloride in form VI by the precipitation method. Valacyclovir hydrochloride is dissolved in a first solvent including an aliphatic monocarboxylic acid and water. The solution is optionally filtered and the filtrate then combined with a second solvent that is a water-miscible ketone to form a suspension which is then cooled. Aliphatic monocarboxylic acids have the formula $RCO_2H$ wherein R is a linear or branched alkyl group having 1 to 6 carbon atoms. The preferred aliphatic monocarboxylic acid is acetic acid, and the preferred water-miscible ketone is acetone.

It is preferred to slowly combine the filtered solution in the first solvent (filtrate_ and the second solvent. Slowly combining means adding small amounts of filtrate, preferably dropwise, over a period of time, preferably from one-half hour to 3 three hours. It is especially preferred to add the filtrate dropwise over about an hour.

Valacyclovir hydrochloride in form VI can be recovered from the suspension by any means known in the art; for example, isolation can be by filtration (gravity or suction) or by centrifugation, to mention just two.

In another embodiment, the present invention provides a method of making valacyclovir hydrochloride in form VI by the precipitation method. For example, BOC-valacyclovir is dissolved in acetic acid and mixed with hydrochloric acid and water. The solution is then filtered and the filtrate added dropwise to acetone to form a suspension which is then cooled.

It is preferred to add one part by weight BOC-valacyclovir to about 2–5, preferably about 3, parts by weight of acetic acid. The mixture is stirred at an elevated temperature (over 38° C.), preferably about 50° C., to dissolve the solids and subsequently cooled to ambient or room temperature, around 25° C. The mixture is maintained under an atmosphere of inert gas, preferably argon. A mixture of about 1 part hydrochloric acid to about 1–4, preferably 2, parts by weight water is then added dropwise over about 1 hour to the mixture of valacylovir and acetic acid.

After being stirred at ambient temperature for about 1 to 4 hours, preferably about 3 hours, the solution is filtered and the resultant filtrate is added over a period of time, preferably about 1 hour, to an amount of acetone that is about 2 to 5 times the volume of filtrate. The suspension is then stirred first for about 1 to 4 hours, preferably 2 hours, at ambient temperature and then for a longer time, 12 to 18 hours, preferably 14 hours, at a cold temperature below −10° C., preferably −15° C.

Typically, valacyclovir hydrochloride in form VI prepared as described above will have a chemical purity of at least about 98% purity.

In another embodiment, the present invention also provides a method of making valacyclovir hydrochloride in form VII by the precipitation method, including the steps of: dissolving valacyclovir HCl in first solvent that is water, filtering the solution, combining the filtered solution with a second solvent that is a water-miscible ketone to obtain a suspension, and then cooling and isolating valacyclovir hydrochloride in form VII. Acetone is the preferred water-miscible ketone.

Valacyclovir hydrochloride in form VII can be isolated from the suspension by any means known in the art. For example, isolation can be by filtration (gravity or suction) or by centrifugation, to mention just two.

Typically, one part by weight valacyclovir hydrochloride is dissolved with about 3–5, preferably about 4, parts by weight of water. The solution is stirred at an elevated temperature above about 38° C., preferably about 40° C., to dissolve the solids. The solids are then filtered. The resultant filtrate is added to an amount of a water-miscible ketone, preferably acetone, equal to about 2 to 6 times the volume of filtrate to form a suspension. The suspension is then stirred first for about 1 to about 4 hours, preferably 2 hours, at a temperature between about 20 and 25° C., preferably about 20° C., and then for a longer time, about 10 to 18 hours, preferably about 12 hours, at a cold temperature below about −10° C., preferably −15° C.

Typically, valacyclovir hydrochloride in form VII prepared as described above has a chemical purity of about 99%.

In still another embodiment, the present invention provides a method for making valacyclovir hydrochloride monohydrate including the steps of contacting a solution of valacyclovir hydrochloride in water with about two to about four times the volume thereof of iso-propanol to form a suspension, stirring the suspension for a stirring period at a temperature below about −10° C., isolating the solid, and drying the solid at reduced pressure to constant weight. The contacting is preferably by mixing with mechanical agitation.

Preferably, the solution and IPA are contacted at a temperature between about 30° C. and about 50° C., preferably at about 40° C. Preferably the temperature during the stirring period is about −15° C. The solid can be isolated from the suspension by any means known in the art, for example filtration.

Methods of Use, Formulations, Dosages

Valacyclovir hydrochloride may be formulated into a variety of pharmaceutical compositions and dosage forms that are useful in treating patients afflicted with viral infections, particularly infections caused by the herpes group of viruses.

In one embodiment, the present invention relates to pharmaceutical compositions including valacyclovir hydrochloride in at least one of forms I, II, IV, V, VI or VII. In addition to the active ingredient(s), valacyclovir hydrochloride pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-DI-SOL®, PRIMELLOSE®)), colloidal silicon dioxide, croscarmellose sodium, crospovidone (e.g. KOLLIDON®), POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl famarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs. An especially preferred dosage form of the present invention is a tablet.

Tablets, capsules, lozenges and other unit dosage forms preferably contain modafinil in a dosage level of from about 50 to about 300 mg, more preferably from about 100 mg to about 200 mg.

The currently marketed form of valacyclovir (VALTREX®) contains valacyclovir hydrochloride equivalent to 500 mg valacyclovir and the inactive ingredients carnauba wax, colloidal silicon dioxide crospovidone, FD&C Blue No. 2 Lake, hydroxypropyl methylcellulose, magnesium stearate, microcrystalline cellulose polyethylene glycol, polysorbate 80, povidone and titanium dioxide.

The function and advantage of these and other embodiments of the present invention will be more fully understood from the examples below. The following examples demonstrate the preparation of various crystalline forms of valacyclovir hydrochloride by the slurry method (examples 1 to 21), the vapor incubation method (examples 22 to 27), and the precipitation method (examples 28 to 32). Preparation of form I by the heating and evaporative method are also illustrated in examples 33 and 34 respectively. These examples are intended to illustrate the benefits of the present invention, but are not intended to limit the scope of the invention.

EXAMPLES

Preparation of Crystalline Forms of Valacyclovir Hydrochloride by the Slurry Method:

Example 1

Valacyclovir hydrochloride (1 g) was suspended in slurry at ambient temperature in ethyl acetate (10 mL) for 24 hours. The mixture was filtered and the isolated solid was dried at 60° C. for 24 hours to give valacyclovir hydrochloride form I.

Example 2

Valacyclovir hydrochloride (1 g) was suspended in slurry at ambient temperature in acetone (10 mL) for 24 hours. The mixture was filtered and the isolated solid was dried at 60° C. for 24 hours to give valacyclovir hydrochloride form I.

Example 3

Valacyclovir hydrochloride (1 g) was suspended in slurry at ambient temperature in methyl ethyl ketone (MEK) (15 mL) for 24 hours. The mixture was filtered and the isolated solid was dried at 60° C. for 24 hours to give valacyclovir hydrochloride form I.

Example 4

Valacyclovir hydrochloride (1 g) was suspended in slurry at ambient temperature in dioxane (15 mL) for 24 hours. The mixture was filtered and the isolated solid was dried at 60° C. for 24 hours to give valacyclovir hydrochloride form I.

Example 5

Valacyclovir hydrochloride (1 g) was suspended in slurry at ambient temperature in methylene chloride (15 mL) for 24 hours. The mixture was filtered and the isolated solid was dried at 60° C. for 24 hours to give valacyclovir hydrochloride form I.

Example 6

Valacyclovir hydrochloride (1 g) was suspended in slurry at ambient temperature in t-butyl methyl ether (15 mL) for 24 hours. The mixture was filtered and the isolated solid was dried at 60° C. for 24 hours to give valacyclovir hydrochloride form I.

Example 7

Valacyclovir hydrochloride (1 g) was suspended in slurry at reflux temperature in t-butyl methyl ether (20 mL) for 24 hours. The mixture was filtered and the isolated solid was dried at 60° C. for 24 hours to give valacyclovir hydrochloride form I.

Example 8

Valacyclovir hydrochloride (1 g) was suspended in slurry at ambient temperature in tetrahydrofurane (THF) (20 mL) for 24 hours. The mixture was filtered and the isolated solid was dried at 60° C. for 24 hours to give valacyclovir hydrochloride form I.

Example 9

Valacyclovir hydrochloride (1 g) was suspended in slurry with a magnetical stirrer at ambient temperature in isopropyl alcohol (10 mL) for 24 hours. The mixture was filtered and the isolated solid was dried at 60° C. for 24 hours to give valacyclovir hydrochloride form II.

Example 10

Valacyclovir hydrochloride (1 g) was suspended in slurry with a mechanical stirrer at ambient temperature in Isopropyl alcohol (15 mL) for 24 hours. The mixture was filtered and the isolated solid was dried at 60° C. for 24 hours to give valacyclovir hydrochloride form II.

Example 11

Valacyclovir hydrochloride (1 g) was suspended in slurry at ambient temperature in 1-butanol (10 mL) for 24 hours. The mixture was filtered and the isolated solid was dried at 60° C. for 24 hours to give valacyclovir hydrochloride form II.

Example 12

Valacyclovir hydrochloride (1 g) was suspended in slurry at ambient temperature in 1-butanol (20 mL) for 24 hours. The mixture was filtered and the isolated solid was dried at 60° C. for 24 hours to give valacyclovir hydrochloride form II.

Example 13

Valacyclovir hydrochloride (1 g) was suspended in slurry at reflux temperature in acetonitrile (25 mL) for 24 hours. The mixture was filtered and the isolated solid was dried at 60° C. for 24 hours to give valacyclovir hydrochloride form II.

Example 14

Valacyclovir hydrochloride (1 g) was suspended in slurry at reflux temperature in methyl ethyl ketone (20 mL) for 22 hours. The mixture was filtered and the isolated solid was dried at 60° C. for 24 hours to give valacyclovir hydrochloride form II.

Example 15

Valacyclovir hydrochloride (1 g) was suspended in slurry at reflux temperature in ethyl acetate (20 mL) for 22 hours. The mixture was filtered and the isolated solid was dried at 60° C. for 24 hours to give valacyclovir hydrochloride form II.

Example 16

Valacyclovir hydrochloride (1 g) was suspended in slurry at ambient temperature in ethanol absolute (15 mL) for 18 hours. The mixture was filtered and the isolated solid was dried at 60° C. for 24 hours to give valacyclovir hydrochloride form II.

Example 17

Valacyclovir hydrochloride (1 g) was suspended in slurry at reflux temperature in Isopropyl alcohol (15 mL) for 24 hours. The mixture was filtered and the isolated solid was dried at 60° C. for 24 hours to give valacyclovir hydrochloride form II.

Example 18

Valacyclovir hydrochloride (1 g) was suspended in slurry at ambient temperature in acetonitrile (20 mL) for 24 hours. The mixture was filtered and the isolated solid was dried at 60° C. for 24 hours to give valacyclovir hydrochloride form II.

Example 19

Valacyclovir hydrochloride (1 g) was suspended in slurry at reflux temperature in acetone (11 mL) for 24 hours. The mixture was filtered and the isolated solid was dried at 60° C. for 24 hours to give valacyclovir hydrochloride form II.

Example 20

Valacyclovir hydrochloride (5 g) was placed in a three neck flask equipped with a Dean-Stark Trap. Toluene (40 mL) was then added and the slurry was heated to reflux temperature. At reflux temperature, toluene (160 mL) and methanol (20 mL) were added. Thirty mL of the solvent were distilled and more methanol added (30 mL). The reaction mixture was refluxed for 45 minutes and the slurry was cooled to ambient temperature, filtered under reduced pressure and dried according to 2 different procedures: (1) by vacuum oven at 50° C. for 24 hours; and, (2) atmospheric oven at 60° C. for 24 hours. Both samples were valacyclovir hydrochloride form II.

Example 21

General procedure: two grams of valacyclovir hydrochloride were stirred in the desired refluxing solvent (200 mL) for 1 hr. The slurry was cooled to room temperature (ca. 25° C.) over a period of about 1 hr. The suspension so obtained was filtered to obtain wet cake. A portion of the wet cake was analysed by x-ray diffraction to determine the polymorphic form. The wet cake was dried in vacuo at 40° C. The water content and polymorphic (crystal) form of the product after the drying step were determined.

The general procedure was repeated with various solvents. The table below lists the polymorph and moisture content obtained with the various solvents, with (d) and without (w) drying.

| Exp. | Solvent | X-Ray Results |
|---|---|---|
| 137-01 w | IPA | IV + III |
| 137-02 d | | IV + II |
| 138-01 w | EtOH | IV |
| 138-02 d | | I |
| 139-01 w | Acetone | IV |
| 139-02 d | | I |
| 140-01 w | THF | IV |
| 140-02 d | | I |

-continued

| Exp. | Solvent | X-Ray Results |
|---|---|---|
| 141-01 w | EtOH/H$_2$O (100:1) | IV >>>> III |
| 141-02 d | | I |
| 142-01 w | EtOH/H$_2$O (100:2) | IV |
| 142-02 d | | I |
| 149-01 d | EtOH/H$_2$O (100:2) | IV |
| 143-01 w | EtOH/H$_2$O (100:5) | IV >>>> III |
| 150-01 d | EtOH/H$_2$O (100:5) | I |
| 144-01 w | IPA/H$_2$O (100:3) | I |
| 144-02 d | | I + II |
| 145-01 w | IPA/H$_2$O (100:8) | IV |
| 145-02 d | | I |
| 148-01 w | BuOH | III |
| 148-02 d | | II |
| 155-01 w | Dioxane | I |
| 155-02 d | | I |
| 161-01-w | MEK | IV |
| 161-02-d | | I |

Preparation of Crystalline Forms of Valacyclovir Hydrochloride by the Vapor Incubation Method:

Example 22

Valacyclovir hydrochloride dry was incubated in a solvent atmosphere of acetonitrile for 1 week. The wet sample was then analyzed by powder X-ray crystallography and shown to be valacyclovir hydrochloride form II.

Example 23

Valacyclovir hydrochloride form I was incubated in controlled humidity cell having a relative humidity of 100% for 1 week to yield valacyclovir hydrochloride form IV dihydrate.

Example 24

Valacyclovir hydrochloride was dissolved in a minimum of hot methanol. The methanol solution was incubated in solvent saturated atmosphere for 32 days in a closed bottle. After 32 days the compounds were crystallized. The procedure was repeated with three different incubating solvents: acetone, ethyl acetate and tetrahydrofuran. In each case, the product obtained was valacyclovir hydrochloride in form III.

Example 25

Valacyclovir hydrochloride was dissolved in a minimum of hot methanol. The methanol solution was incubated in butanol atmosphere for 32 days in a closed bottle. After 32 days the compounds were crystallized, yielding valacyclovir hydrochloride form III. The procedure was repeated with two different incubating solvents: ethanol abs., butanol. The product obtained was valacyclovir hydrochloride in form III.

Example 26

Valacyclovir hydrochloride dry was incubated in a solvent atmosphere of ethanol for 1 week. Then the wet sample was analyzed and shown to be valacyclovir hydrochloride form III.

Example 27

Valacyclovir hydrochloride dry was incubated in a solvent atmosphere of methanol for 1 week. Then the wet sample was analyzed and shown to be valacyclovir hydrochloride form III.

Preparation of Crystalline Forms of Valacyclovit Hydrochloride by the Precipitation Method:

Example 28

General Procedure: Three Grams of Valacyclovir hydrochloride were dissolved in 18 mL of first solvent at about 25° C. The solution was stirred and 300 mL of second solvent were added to the solution. A suspension of a white solid precipitate of valacyclovir hydrochloride was formed.

The suspension was stirred 1 hr and filtered to recover wet cake precipitate. A portion of the wet cake precipitate was analysed by x-ray diffraction to determine the polymorphic form. The wet cake was dried in vacuo at 40 C. The water content and polymorphic form of the dried material were determined.

Table A gives the results obtained with several second solvents when water was the first solvent. Table B gives the results obtained with water as the second solvent.

A

| Exp. | Solvent | Water content (%) | X-Ray Results |
|---|---|---|---|
| 147-01 w | ACN | | IV |
| 147-02 d | | 9.22 | I |
| 152-01 w | BuOH | | IV |
| 152-02 d | | 5.74 | I |
| 154-01 w | Acetone | | IV |

B

| Exp. | Solvent | Water content (KF, %) | X-Ray Results |
|---|---|---|---|
| 151-01 w | ACN | | IV |
| 151-02 d | | 6.85 | I |
| 153-01 w | BuOH | | IV |
| 153-02 d | | 8.72 | I |

Example 29

Reagents:

| t-BOC Valacyclovir, F.W. 424.45 | 4.5 g |
| | (10.5 mmol) |
| Hydrochloric acid, 37%, F.W. 36.46 | 4 mL |
| | (47.3 mmol) |
| Water, F.W. 18.02 | 19 mL |

Thirty-seven percent hydrochloric acid (4 mL) was added dropwise, during 10 min to a suspension of t-BOC-valacyclovir (4.5 g) in Water (19 mL) at 20–25° C. The reaction mixture was stirred for about 5 h at 20–25° C., cooled with ice water, followed by addition of IPA to this mixture to give a white precipitate. The suspension was stirred for about 1 h at T<10° C. (ice water bath) and kept at 4° C. overnight. The precipitate was filtered off, washed with cold IPA (20 mL) and dried to give valacyclovir HCl in form V(2.6 g, 68%), 97.7% pure by HPLC, 4.07% of D-isomer.

Example 30

Reagents:

| t-BOC Valacyclovir F.W. 424.45 | 9.0 g |
| | (21.0 mmol) |
| Hydrochloric acid, 37%, F.W. 36.46 | 8 mL |
| | (94.6 mmol) |
| Water, F.W. 18.02 | 22 mL |

A mixture of t-BOC-valacyclovir (9.0 g, 21 mmol) and water (22 mL) was stirred for about 20 min. to obtain a fine suspension. 37% hydrochloric acid (8 mL) was added dropwise to this suspension at 20–25° C., the reaction mixture was stirred for about 3.5 h at 20–25° C., cooled with ice water, followed by addition of IPA (500 mL) to give a white precipitate. The suspension was stirred for about 1 h at T<10° C. (ice water bath) and kept at 4° C. overnight. The white precipitate was filtered off, dried under reduced pressure to give valacyclovir HCl in form V (7.0 g, 92%), 97.9% pure by HPLC, 4.0% of D-isomer.

Example 31

A 250-mL double-jacketed reactor was charged with BOC-valacyclovir (15.0 g) and acetic acid (45.0 g) and filled with argon. The obtained mixture was stirred at 50° C. to complete dissolution of all solids and cooled to 25° C. A mixture of 37% hydrochloric acid (13.9 g) and water (30.0 g) was added dropwise over one hour and the solution was stirred for 3 hours at 20–25° C. The reaction mixture was filtered and the filtrate was added dropwise at 25° C. over a period of one hour to acetone (188 g). The suspension was then stirred for 2 hours at 25° C. and then at 14 hours at −15° C. The precipitate was filtered off, washed on the filter with cold acetone (28 g) to obtain 19.1 g of wet product which was dried under reduced pressure at 25° C. to a constant weight to give 10.8 g (84.9%) of valacyclovir hydrochloride in form VI with 98.67% purity by HPLC. Both the wet and dry products contain valacyclovir hydrochloride in form VI, as characterized by X-ray powder diffraction.

Example 32

A 50-mL reactor was charged with a crude valacyclovir HCL (8.8 g) and water (35.2 g). The obtained mixture was stirred at 40° C. to complete dissolution of all solids and a solution was filtered. The filtrate was added to acetone (132 g) at 40° C., a suspension was stirred for 2 hours at 20° C. and 12 hours at −15° C. The precipitated solid was filtered off, washed on the filter with cold acetone (20 g) to give valacyclovir hydrochloride form VII, as characterized by X-ray powder diffraction. This method produced valacyclovir hydrochloride in form VII with 99% purity by HPLC.

Preparation of Valacyclovir Form I by the Thermal Method:

Example 33

Valacyclovir hydrochloride form IV was dried to constant at reduced pressure at 40–50° C. Analysis of the sampel showed it to be form I.

Preparation of Valacyclovir Form I by the Evaporative Method:

Example 34

Two grams of valacyclovir hydrochloride were dissolved in 250 mL of methanol at 40° C. The methanol was evaporated at 40° C. under reduced pressure to obtain form I.

Preparation of Valacyclovir Monohydrate by a Precipitation Method

Example 35

A 1 L reactor was charged with crude valacyclovir hydrochloride (180 g) and water (720 g). The mixture was heated to and stirred at about 40° C. to effect dissolution of the solids. The solution was filtered and the filtered solution was added to 2-propanol (2700 g) in a 6L double-jacketed reactor at 40° C. to form a suspension. The suspension formed was stirred for 2 hours at 25° C. and the 4 hours at −15° C. The precipitated solids were collected by filtration, washed with cold 2-propanol (1440 g) and dried to constant weight under reduced pressure to yield 148.5 g (82.5%) of valacyclovir monohydrate with 99.52 area-% purity by HPLC, assay 96.7% by $HClO_4$ titration assay, assay 95.0% by AgNO3 titration. The water content (Karl-Fisher) of the product was 3.45%. The loss on drying (TGA) was 4.5%.

We claim:

1. Valacyclovir hydrochloride sesquihydrate.
2. A method of making valacyclovir hydrochloride form II comprising the step of slurrying valacyclovir hydrochloride in a slurry solvent selected from the group consisting of isopropyl alcohol, 1-butanol, and ethanol.
3. The method of claim 2 wherein the slurry solvent is isopropyl alcohol.
4. A method of making valacyclovir hydrochloride formII comprising the steps of:
   a, slurrying valacyclovir in a slurry solvent selected from acetonitrile, methyl ethyl ketone, ethyl acetate, acetone, and toluene
   b, heating the slurry to reflux,
   c, refluxing the resulting mixture, and
   d, isolating valacyclovir hydrochloride in form II from the mixture.
5. The method of claim 4 wherein the slurry solvent is toluene and further comprising the step of adding methanol to the refluxing mixture of valacyclovir hydrochloride and toluene.
6. The method of claim 5 further comprising the step of drying the isolated valacyclovir hydrochloride form II at a temperature of about 60° C.
7. The method of claim 3 further comprising the step of drying the isolated valacyclovir hydrochloride form II at a pressure less than about 500 mm Hg and the temperature is about 50° C.
8. A method of making valacyclovir in form III comprising the step of incubating valacyclovir hydrochloride in an atmosphere saturated with vapors of at least one incubating solvent selected from the group consisting of isopropanol, ethanol, butanol, acetone, ethyl acetate, terahydrofuran, acetonitrile, and methanol.
9. The method of claim 8 wherein the valacyclovir hydrochloride is in solution in the incubating solvent.
10. The method of claim 8 wherein the valacyclovir hydrochloride is in solid form and the incubating solvent is acetonitrile.
11. A method of making valacyclovir hydrochloride form IV comprising the step of incubating valacyclovir hydrochloride in an atmosphere saturated with vapors of an incubating solvent that is water.
12. The method of claim 11 wherein the incubating solvent is water and the atmosphere has a relative humidity of about 100%.
13. A method of making valacyclovir in form VI comprising the step of mixing a solution of valacyclovir hydrochloride in a first solvent comprising water and an aliphatic monocarboxylic acid, with a second solvent comprising a water-miscible ketone to form a suspension.
14. The method of claim 13 wherein the first solvent comprises between about 30% and about 60% by volume of water and wherein the amount of the second solvent is about 2 to about 5 times the volume of said first solvent.
15. The method of claim 13 wherein the water-miscible ketone is acetone.
16. The method of claim 13 further comprising the step of filtering the solution of valacyclovir hydrochloride in first solvent before the mixing step.
17. The method of claim 13 further comprising the steps of;
   agitating the suspension at a temperature less than about −10° C. and
   isolating valacyclovir hydrochloride in form VI from the suspension.
18. A method of making valacyclovir hydrochloride in form VII comprising the step of mixing a solution of valacyclovir hydrochloride in a first solvent consisting essentially of water with a second solvent comprising a water-miscible ketone to form a suspension.
19. The method of claim 18 wherein the water-miscible ketone is acetone.
20. The method of claim 18 further comprising the steps of:
   agitating the suspension at a temperature less than about −10° C.; and
   isolating valacyclovir hydrochloride in form VII from the suspension.
21. A method of making valacyclovir hydrochloride monohydrate comprising the step of contacting a solution of valacyclovir hydrochloride in water with iso-propanol to form a suspension.
22. The method of claim 21 wherein the contacting is at a temperature of between about 30° C. and about 50° C.
23. The method of claim 22 wherein the contacting is at a temperature of about 40° C.
24. The method of claim 21 further comprising the steps of isolating the solid from the suspension and drying the isolated solid at a temperature of about 25° C. to constant weight.
25. The method of claim 24 wherein the drying is at reduced pressure.
26. Valacyclovir hydrochloride dihydrate.

* * * * *

UNITED STATES PATENT AND TRADEMARK OFFICE
CERTIFICATE OF CORRECTION

PATENT NO. : 6,849,736 B2
DATED : February 1, 2005
INVENTOR(S) : Wizel et al.

It is certified that error appears in the above-identified patent and that said Letters Patent is hereby corrected as shown below:

Column 2,
Line 5, change "guanosine" to -- guanine --
Line 30, change "Dimethylform amide" to -- dimethylformamide --

Column 4,
Line 35, change "stochiometric" to -- stoichiometric --

Column 6,
Lines 9, 16 and 50, change "tetrahydrofurane" to -- tetrahydrofuran --
Line 35, change "acetonitrille" to -- acetonitrile --

Column 8,
Line 22, change "was" to -- were --
Line 65, change "impuruty" to -- impurity --

Column 9,
Line 41, change "thermal thermal" to -- thermal --

Column 12,
Lines 14 and 51, change "tetrahydrofurane" to -- tetrahydrofuran --

Column 15,
Line 47, change "pregelitinized" to -- pregelatinized --

Column 16,
Line 16, change "dixoide" to -- dioxide --
Lines 21, 23 and 26, change "dye" to -- die --
Line 31, change "famarate" to -- fumarate --

Column 18,
Line 7, change "tetrahydrofurane" to -- tetrahydrofuran --
Line 15, change "magnetical" to -- magnetic --

Column 20,
Line 66, change "Valacyclovit" to -- Valacyclovir --

Column 22,
Line 58, change "sampel" to -- sample --

UNITED STATES PATENT AND TRADEMARK OFFICE
CERTIFICATE OF CORRECTION

PATENT NO. : 6,849,736 B2
DATED : February 1, 2005
INVENTOR(S) : Wizel et al.

It is certified that error appears in the above-identified patent and that said Letters Patent is hereby corrected as shown below:

Column 23,
Line 27, change "formII" to -- form II --

Signed and Sealed this

Twelfth Day of July, 2005

JON W. DUDAS
*Director of the United States Patent and Trademark Office*